United States Patent
Buus

(10) Patent No.: US 9,592,147 B2
(45) Date of Patent: Mar. 14, 2017

(54) OSTOMY APPLIANCE

(75) Inventor: Hasse Buus, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 316 days.

(21) Appl. No.: 13/814,248

(22) PCT Filed: Aug. 16, 2011

(86) PCT No.: PCT/DK2011/050311
§ 371 (c)(1),
(2), (4) Date: Feb. 5, 2013

(87) PCT Pub. No.: WO2012/022354
PCT Pub. Date: Feb. 23, 2012

(65) Prior Publication Data
US 2013/0138065 A1    May 30, 2013

(30) Foreign Application Priority Data

Aug. 16, 2010   (DK) .............................. 2010 70362
Aug. 16, 2011   (WO) ................ PCT/DK2011/050311

(51) Int. Cl.
| | | |
|---|---|---|
| *A61F 5/44* | (2006.01) | |
| *A61F 5/443* | (2006.01) | |
| *A61M 1/00* | (2006.01) | |
| *A61F 5/448* | (2006.01) | |
| *A61F 13/00* | (2006.01) | |
| *A61F 5/445* | (2006.01) | |

(52) U.S. Cl.
CPC ............... *A61F 5/443* (2013.01); *A61F 5/44* (2013.01); *A61F 5/445* (2013.01); *A61F 5/4408* (2013.01); *A61F 5/448* (2013.01); *A61F 2013/00608* (2013.01)

(58) Field of Classification Search
CPC ............ A61F 5/443; A61F 2013/00608; A61F 5/445; A61F 5/448; A61F 5/44; A61F 5/4408
USPC ................................. 604/344, 540, 338, 339
See application file for complete search history.

(56) References Cited

U.S. PATENT DOCUMENTS

| | | | | |
|---|---|---|---|---|
| 5,362,420 | A * | 11/1994 | Itoh .................... | A61B 5/04087 252/500 |
| 5,722,965 | A * | 3/1998 | Kuczynski .................... | 604/344 |
| 6,000,726 | A * | 12/1999 | Campbell ...................... | 283/81 |
| 6,579,271 | B1 | 6/2003 | Aruffo et al. | |
| 2003/0004477 | A1 | 1/2003 | Nielsen et al. | |
| 2003/0171737 | A1* | 9/2003 | Leise et al. ................... | 604/540 |
| 2009/0148503 | A1* | 6/2009 | Trieu ............................ | 424/447 |

(Continued)

FOREIGN PATENT DOCUMENTS

| | | |
|---|---|---|
| EP | 1020198 | 7/2006 |
| RU | 2060035 C1 | 5/1996 |

(Continued)

*Primary Examiner* — Tatyana Zalukaeva
*Assistant Examiner* — Andrew J Mensh
(74) *Attorney, Agent, or Firm* — Coloplast Corp., Coloplast A/S; Nick Baumann

(57) ABSTRACT

The present invention discloses an ostomy device comprising an adhesive wafer, wherein said adhesive wafer comprises means for preventing deformation and tearing when the adhesive wafer is removed from the skin. In particular, the present invention relates to adhesive wafers formed of soft adhesives.

7 Claims, 1 Drawing Sheet

(56) References Cited

U.S. PATENT DOCUMENTS

2010/0204665 A1\* 8/2010 Stroebech ............... A61F 5/443
  604/344
2011/0213321 A1\* 9/2011 Fattman et al. ............. 604/344

FOREIGN PATENT DOCUMENTS

| RU | 2118145 C1 | 8/1998 |
| WO | 03074808 A1 | 9/2003 |
| WO | 03075808 | 9/2003 |
| WO | 2007121744 | 11/2007 |
| WO | 2009075636 | 6/2009 |
| WO | 2009075636 A1 | 6/2009 |

\* cited by examiner

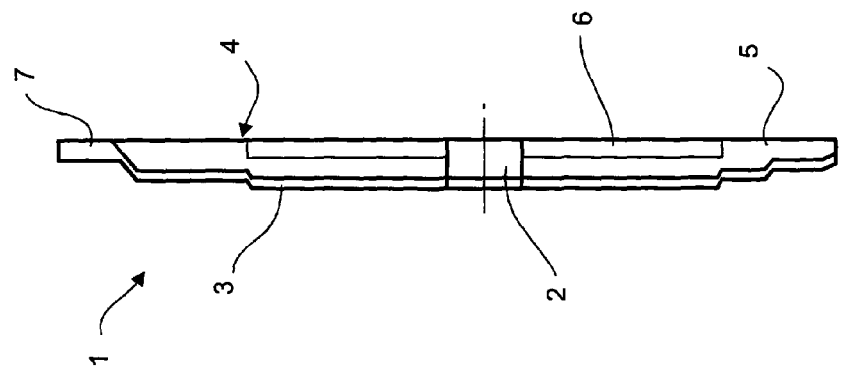
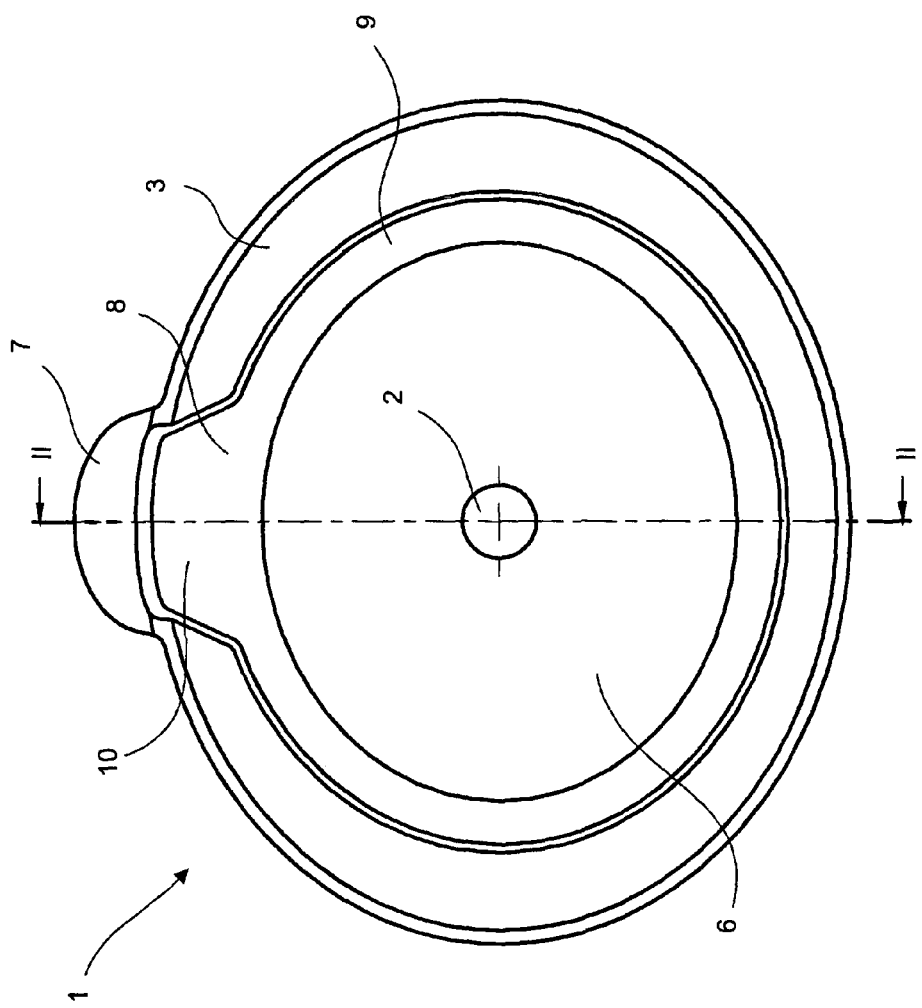

OSTOMY APPLIANCE

The present invention discloses an ostomy device comprising an adhesive wafer, wherein said adhesive wafer comprises means for preventing deformation and tearing when the adhesive wafer is removed from the skin. In particular, the present invention relates to adhesive wafers formed of soft adhesives.

BACKGROUND

Collecting devices for collecting bodily waste, ostomy appliances, wound or fistulae drainage bandages or devices for collecting urine are usually in the form of a receptacle, e.g. a bag, pouch or tube for receiving the waste, connected to an adhesive wafer that can be attached to the user's skin. The wafer is typically in the form of a backing layer coated on the skin-facing surface with an adhesive layer, and the wafer may further be provided with an aperture for accommodating the body opening. The size and shape of said aperture can often be adapted individually to fit the anatomy of the patient.

One of the crucial parts of such devices is the adhesive wafer. The wafer should be able to fit leak proof around the body opening and have good adherence to the skin without unintended detachment from the skin, but at the same time the wafer should be easy to remove again without damaging the skin. Furthermore, the wafer should be able to follow the movements of the body and be comfortable to wear. The components of the wafer, the adhesive and the backing layer determine these properties.

Pressure sensitive adhesives have for a long time been used for attaching medical devices, such as ostomy appliances, dressings (including wound dressings), wound drainage bandages, fistula drainage devices, devices for collecting urine, orthoses and prostheses to the skin.

The adhesive of such devices is usually a hydrocolloid adhesive coated in a relatively thick layer on a backing layer, and combined with the fact that this adhesive is rather stiff, the device may be inflexible and bulky to wear.

Ostomy wafers with softer adhesives are already known. These have been developed in order to solve some of the above problems such as inflexibility and bulkiness. Such soft adhesives may for example be silicone adhesives. Although such adhesives solve problems regarding comfort due to their softness they may be complicated to remove from the skin. Being soft and flexible, they stretch and are difficult to control. In some cases they may even tear during removal from the skin.

Thus, there exists a need to reduce the risk that the adhesive wafer is greatly deformed or torn when removed from the skin.

DETAILED DESCRIPTION OF THE PRESENT INVENTION

The invention discloses an adhesive wafer for removable placement on the skin surface of a mammal, the adhesive wafer comprising a backing layer whereon at least a first adhesive is disposed in a first adhesive layer, the adhesive wafer extending mainly in one plane from a center of the adhesive wafer in a radial direction towards an annular peripheral edge of the adhesive wafer, the radial extent being larger than the axial extent, wherein a pulling tab is provided at the annular peripheral edge and that reinforcement means are provided only between the center and the pulling tab.

This allows the adhesive wafer to maintain most of its flexibility, while providing an area of the adhesive with improved resistance to deformation and thereby tearing when removing the adhesive wafer from the skin. The reinforcement means are advantageously arranged between the pull tab and the center of the adhesive wafer in a radial direction towards the pull tab. The pull tab provides a clear indication of where to pull when removing the wafer and also facilitates gripping, while the reinforcement means provides the added support to allow easy removal of the wafer.

The reference to the center of the adhesive wafer should be understood broadly as a central point or area of the wafer which would be considered central when considering the wafer either geometrically, by mass or otherwise indicates the middle of the wafer. For example, if considering an ostomy base plate the hole for receiving the stoma would be considered the center of the adhesive wafer. The reinforcement means does not necessarily have to extend all the way from the center to the tab, but may in some embodiments extend partly in the radial direction from the center of the first adhesive layer towards the peripheral edge of the adhesive wafer.

In one embodiment, the reinforcement means are provided as an area of the first adhesive having a larger thickness than the adjacent first adhesive layer. This is a simple way of providing improved strength in an area and thereby reducing the risk of tearing.

In another, or additional, embodiment, the reinforcement means are provided in the form of a material having greater tear strength than the adjacent first adhesive layer and the backing layer. This allows for very high resistance to tearing because materials may be chosen that are very tear resistant while at the same time being highly flexible.

One such material may for example be a mesh. Providing a mesh between the backing layer and the adhesive would have the advantage that manufacturing was facilitated as the openings in the mesh would allow the adhesive to effectively bond to the backing layer.

In some embodiments of adhesive wafers, two or more different adhesives are used in order to achieve the different advantages of these adhesives. Thus, in another embodiment, a second adhesive is disposed on the first adhesive layer as a second adhesive layer, the second adhesive layer extending only partly from the center of the adhesive wafer towards the peripheral edge of the adhesive wafer, wherein the reinforcement means is thicker than the first adhesive layer. Typically it is the thinnest adhesive layer which has a risk of tearing. Thus, by at least providing reinforcement with a thickness greater than the thinnest layer, resistance to tearing is improved.

In other embodiments the reinforcement means may for example comprise at least one string extending in a radial direction between the center and the pulling tab. The at least one string may have a lower elasticity than the part of the wafer which do not extend between the center and the pulling tab.

Thus the string determines the deformation and/or tear strength of the wafer in the area between the pull tab and the center of the wafer.

In another aspect the present invention relates to a kit comprising an adhesive wafer for removable placement on the skin surface of a mammal, the adhesive wafer comprising a backing layer whereon at least a first adhesive is disposed in a first adhesive layer, the adhesive wafer extending mainly in one plane from a center in a radial direction towards an annular peripheral edge, the radial extent being larger than the axial extent, wherein a pulling tab is provided at the annular peripheral edge, and an adhesive label for attachment to the adhesive wafer between the pull tab and the center.

By providing the reinforcement means as a separate adhesive label the user can apply the label before removal of the wafer. Thus the increased material and stiffness that the reinforcement means may add to the wafer can be avoided during use.

FIGURES

FIG. 1 illustrates an adhesive wafer as described herein.

FIG. 2 shows in section the adhesive wafer of FIG. 1 along line II-II.

DETAILED DESCRIPTION

The figures show an adhesive wafer 1 for application to the skin surrounding a stoma. The adhesive wafer has a central through-going hole 2 which can be cut into shape if necessary in order to receive a stoma.

The adhesive wafer is formed of a backing layer 3, whereon an adhesive 4 is arranged on the proximal side. In use the proximal side is the side facing the user, thereby exposing the adhesive to the skin and adhering it thereto. The distal side of the adhesive wafer faces away from the skin providing a non-adhesive surface preventing that unwanted articles, such as clothing, adheres to the wafer.

The distal side is also provided with collection means (not shown). Such collection means may be a collecting bag attached directly to the backing layer. However, other arrangements such as coupling elements for allowing a detachable connection to a collecting bag may be provided. Such arrangements have not been shown in order to simplify the illustration and also because these are already well known in the art and not part of the present invention.

A pull tab 7 is provided along the periphery of the adhesive wafer. The pull tab 7 provides the user with means for easily getting hold of the adhesive wafer in order to remove it from the skin.

The adhesive 4 is formed of two adhesive layers. A first adhesive layer 5 is disposed on and covers the proximal side of the backing layer 3. A second adhesive layer 6 is disposed on the proximal surface side of the first adhesive layer. The second adhesive layer encircles the through-going hole and has a smaller radial extent than the first adhesive layer. By providing two adhesive layers, different properties can be accentuated. For example, the second adhesive layer 6 can be formed of an adhesive having high hydrocolloid content. This allows it to absorb moisture and small amounts of output from and around the stoma. The first adhesive layer can however be formed to have a high tack giving it a higher resistance to peeling.

In order to provide a comfortable feel when wearing the adhesive wafer, and further prevent pressure wounds and the like, the adhesive wafer is made as soft as possible. By 'soft' is meant that the adhesive wafer is highly flexible and stretchable in order to follow the movement of the skin whereon it is adhered. A number of elements can be manipulated in order to provide such a 'soft' feel. For example the backing layer 3 is formed of a flexible and stretchable material and the adhesive 4 is made as thin as possible.

However, as the softness of the adhesive wafer is increased the adhesive wafer becomes more difficult to remove from the skin. This is due to the high stretchability of the adhesive wafer which results in that instead of being easily removed, the adhesive wafer stretches and deforms making it difficult to handle. In some cases, the adhesive wafer simply tears apart when the user tries to remove it from the skin.

Thus, in order to prevent excessive deformation or even tearing, a reinforced area 8 has been provided. In the shown embodiment, the reinforced area 8 is provided by increasing the thickness of the first adhesive layer in some areas. In particular the inner annular area 9 of the first adhesive layers has been made thicker and a lip 10 in the form of a strip of adhesive having increased thickness is provided between the inner annular area and the pulling tab 7.

Thus, the stability of the adhesive wafer is increased allowing it to be removed by pulling the pull tab 7 without the risk of excessively deforming or tearing the adhesive wafer while at the same time maintaining most of the softness of the adhesive wafer.

As discussed previously, other means of providing stability when pulling the pull tab 7 may be provided. Thus, instead of increasing the thickness of the material a reinforcement material could be provided between the through-going hole and the pull tab. The reinforcement material could for example be in the shape of a mesh and it could be dimensioned so as to have a desired stretchability so that it can be elongated to a certain extent without tearing.

The invention claimed is:

1. An adhesive wafer for removable placement onto skin, the adhesive wafer comprising:
    a backing layer with a stoma receiving hole formed in the backing layer;
    a first adhesive layer disposed on the backing layer around the stoma receiving hole and a second adhesive layer disposed on the first adhesive layer and around the stoma receiving hole, with a radial extent of the first adhesive layer from the stoma receiving hole being larger than a radial extent of the second adhesive layer from the stoma receiving hole;
    a pulling tab providing an outermost peripheral edge of the adhesive wafer, with the pulling tab abutting the first adhesive layer;
    the first adhesive layer comprising a reinforced area provided by an inner annular area connected to a lip portion, with the inner annular area formed around the second adhesive layer and the lip portion extending in a radial direction from the inner annular area to the pulling tab;
    wherein a first thickness of the first adhesive layer at the inner annular area and at the lip portion is greater than a second thickness of the first adhesive layer outside of the reinforced area.

2. An adhesive wafer according to claim 1, wherein an outer perimeter of the lip portion extends along an arc having an arc length less than an entirety of a perimeter of the adhesive wafer.

3. An adhesive wafer according to claim 1, wherein the first adhesive layer has a higher tack than the second adhesive layer, and the second adhesive layer is more moisture absorbing than the first adhesive layer.

4. The adhesive wafer according to claim 1, wherein the first adhesive layer in the reinforced area is disposed to comprise a transition between the inner annular area and the lip portion defining an angle of approximately 135°.

5. The adhesive wafer according to claim 2, wherein the arc length of the outer perimeter of the lip portion is a first arc length that constitutes less than an entirety of a second arc length of the pulling tab wherein it is abutting the first adhesive layer.

6. The adhesive wafer according to claim 2, wherein the arc of the outer perimeter of the lip portion is coincident with an outer peripheral edge of the backing layer.

7. The adhesive wafer according to claim 1, wherein the backing layer is made from a stretchable material.

* * * * *